US012678557B2

(12) United States Patent
Yakushiji

(10) Patent No.: US 12,678,557 B2
(45) Date of Patent: Jul. 14, 2026

(54) DRUG SOLUTION ADMINISTRATION DEVICE

(71) Applicant: TERUMO KABUSHIKI KAISHA, Tokyo (JP)

(72) Inventor: Yusuke Yakushiji, Atsugi (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 973 days.

(21) Appl. No.: 17/945,244

(22) Filed: Sep. 15, 2022

(65) Prior Publication Data

US 2023/0014779 A1      Jan. 19, 2023

Related U.S. Application Data

(63) Continuation of application No. PCT/JP2021/009189, filed on Mar. 9, 2021.

(30) Foreign Application Priority Data

Mar. 25, 2020    (JP) ................................. 2020-054542

(51) Int. Cl.
$A61M\ 5/145$      (2006.01)
$A61M\ 5/142$      (2006.01)
(Continued)

(52) U.S. Cl.
CPC .......... *A61M 5/1456* (2013.01); *A61M 5/162* (2013.01); *A61M 5/16831* (2013.01); *A61M 2205/3365* (2013.01)

(58) Field of Classification Search
CPC ............... A61M 5/1456; A61M 5/162; A61M 5/16831; A61M 2205/3365;
(Continued)

(56) References Cited

U.S. PATENT DOCUMENTS

2003/0205587 A1   11/2003   Tribe et al.
2007/0066938 A1   3/2007   Iio et al.
(Continued)

FOREIGN PATENT DOCUMENTS

CN      103228303 A     7/2013
CN      109451731       3/2019
(Continued)

OTHER PUBLICATIONS

English Translations of the International Search Report (Form PCT/ISA/210) and the Written Opinion of the International Searching Authority (Form PCT/ISA/237) issued May 11, 2021, by the Japan Patent Office in corresponding International Application No. PCT/JP2021/009189. (6 pages).
(Continued)

*Primary Examiner* — Jason E Flick
(74) *Attorney, Agent, or Firm* — Buchanan Ingersoll & Rooney PC

(57) ABSTRACT

A drug solution administration device that detects an administration condition of a drug solution with higher accuracy. The drug solution administration device includes a pusher, a drive mechanism configured to move the pusher forward and backward with respect to a distal end opening of the drug solution container, and a control unit configured to control operation of the drive mechanism. The drive mechanism includes a motor configured to generate driving force for moving the pusher forward and backward, and a rotation detection unit configured to detect rotation of the motor. The control unit has an operation confirmation function of confirming an operating condition of the motor on the basis of a detection result of the rotation detection unit. After confirming that the motor is stopped by the operation confirmation function, the control unit starts reverse rotation of the
(Continued)

10 motor to determine whether or not the pusher moves backward.

12 Claims, 8 Drawing Sheets

(51) Int. Cl.

| | | |
|---|---|---|
| *A61M 5/162* | (2006.01) | |
| *A61M 5/168* | (2006.01) | |
| *A61M 5/172* | (2006.01) | |

(58) Field of Classification Search
CPC .......... A61M 2005/16863; A61M 2205/3327; A61M 5/172; A61M 5/14244; A61M 5/145; A61M 5/1452; A61M 5/14208; A61M 5/14566; A61M 5/14248
See application file for complete search history.

(56) References Cited

U.S. PATENT DOCUMENTS

| | | | |
|---|---|---|---|
| 2012/0078184 A1* | 3/2012 | Smith | .............. A61M 5/16854 604/152 |
| 2012/0078217 A1 | 3/2012 | Smith et al. | |
| 2012/0078222 A1 | 3/2012 | Smith et al. | |
| 2012/0192951 A1 | 8/2012 | Yodfat et al. | |
| 2015/0133855 A1 | 5/2015 | Smith et al. | |
| 2019/0217007 A1 | 7/2019 | Sasaki | |
| 2021/0008274 A1 | 1/2021 | Kondo et al. | |
| 2021/0299349 A1 | 9/2021 | Tada | |

FOREIGN PATENT DOCUMENTS

| | | | | |
|---|---|---|---|---|
| JP | 2002113099 A | 4/2002 | | |
| JP | 2013537844 A | 10/2013 | | |
| JP | 2015181869 A | 10/2015 | | |
| WO | WO-2018061562 A1 * | 4/2018 | ............ | A61M 5/168 |
| WO | 2019/189703 A1 | 10/2019 | | |
| WO | 2020/031910 A1 | 2/2020 | | |

OTHER PUBLICATIONS

International Search Report (PCT/ISA/210) with translation and Written Opinion (PCT/ISA/237) mailed on May 11, 2021, by the Japan Patent Office as the International Searching Authority for International Application No. PCT/JP2021/009189. (9 pages).

The Extended European Search Report issued Jul. 5, 2023, by the European Patent Office in corresponding European Patent Application No. 21776826.6-1122. (8 pages).

Office Action/Search Report (The First Office Action) issued on Mar. 17, 2025, in corresponding Chinese Patent Application No. 202180007376.3 and English translation of the Office Action. (23 pages).

\* cited by examiner

DRUG SOLUTION ADMINISTRATION DEVICE

CROSS-REFERENCES TO RELATED APPLICATIONS

This application is a continuation of International Application No. PCT/JP2021/009189 filed on Mar. 9, 2021, which claims priority to Japanese Application No. 2020-054542 filed on Mar. 25, 2020, the entire content of both of which is incorporated herein by reference.

TECHNOLOGICAL FIELD

The present disclosure generally relates to a drug solution administration device.

BACKGROUND DISCUSSION

In related art, a syringe pump type drug solution administration device that administers a drug solution filled in a drug solution container into a living body by pressing action of a pusher is known. The drug solution administration device includes a drive mechanism including a motor configured to generate driving force, and a control unit configured to control the drive mechanism.

In a drug solution administration device, a drive mechanism causes a pusher to move forward little by little to administer a drug solution to a living body. Thus, if the pusher is stopped, administration of the drug solution is also stopped. However, in a case of a drug solution administration device that determines that administration of a drug solution is completed when a motor is stopped (a pusher is stopped), there is a possibility that it is determined that administration of the drug solution is completed also when the motor is stopped due to an abnormality (for example, motor failure) occurring in the device.

SUMMARY

A drug solution administration device is disclosed that detects an administration condition of a drug solution with higher accuracy.

A drug solution administration device of the present disclosure includes a pusher configured to push a drug solution in a drug solution container filled with the drug solution, a drive mechanism configured to cause the pusher to move forward and backward with respect to a distal end opening of the drug solution container, and a control unit configured to control operation of the drive mechanism, in which the drive mechanism includes a motor configured to generate driving force for moving the pusher forward and backward, and a rotation detection unit configured to detect rotation of the motor, the control unit has an operation confirmation function of confirming an operating condition of the motor on the basis of a detection result of the rotation detection unit, and the control unit starts reverse rotation of the motor to determine whether or not the pusher moves backward after confirming that the motor is stopped by the operation confirmation function.

A drug solution administration device of the present disclosure includes a drug solution container filled with a drug solution; a gasket configured to be slidable on an inner wall in the drug solution container; a pusher configured to push the gasket; a drive mechanism configured to move the pusher forward and backward with respect to a distal end opening of the drug solution container; a control unit configured to control operation of the drive mechanism; wherein the drive mechanism includes a motor configured to generate driving force for moving the pusher forward and backward, and a rotation detection unit configured to detect rotation of the motor; the control unit including an operation confirmation function configured to confirm an operating condition of the motor on the basis of a detection result of the rotation detection unit; and the control unit is configured to determine whether or not the pusher is in contact with the gasket by reversely rotating the motor to cause the pusher to move backward and subsequently rotating the motor forward after confirming that the motor is stopped by the operation confirmation function.

A method for detecting an administration of a drug solution from a drug solution container of the present disclosure includes detecting a rotation of a motor, the rotation of the motor generating a driving force to move a pusher forward and backward within the drug solution container; confirming an operating condition of the motor based on the detected rotation of the motor; and determining whether or not the pusher moves backward after confirming that the motor is stopped by the operation confirmation function for detection of an administration condition of the drug solution.

According to a drug solution administration device of the present disclosure, after confirming that a motor is stopped, a control unit starts reverse rotation of the motor to determine whether or not a pusher moves backward. As a result, the control unit can confirm an operating condition of the motor and determine whether or not an administration abnormality of a drug solution occurs due to a failure of the motor. Thus, the drug solution administration device can detect an administration condition of the drug solution with higher accuracy.

BRIEF DESCRIPTION OF THE DRAWINGS

FIG. 7 is a view schematically illustrating a rotation detection unit, and the like.

DETAILED DESCRIPTION

Figure 1:
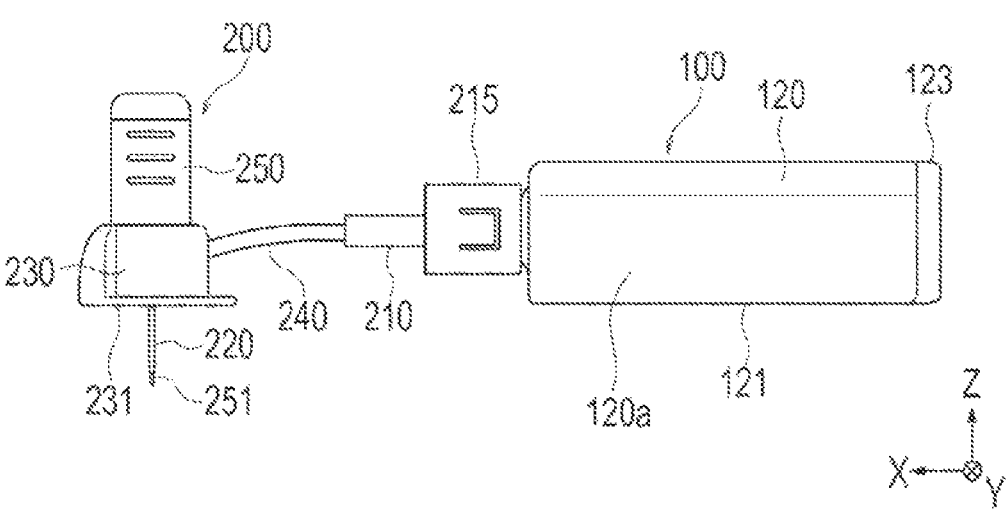
FIG. 1 is a side view of a drug solution administration system according to the present embodiment.

Set forth below with reference to the accompanying drawings is a detailed description of embodiments of a drug solution administration device. Note that since embodiments described below are preferred specific examples of the present disclosure, although various technically preferable limitations are given, the scope of the present disclosure is not limited to the embodiments unless otherwise specified in the following descriptions. In addition, dimensional ratios in the drawings are exaggerated for convenience of description and may be different from actual ratios.

FIGS. 1 to 8B are views for explaining a drug solution administration system 10, a drug solution administration device 100, and an administration instrument 200 according to an embodiment. An arrow X in each figure indicates a "longitudinal direction (longitudinal direction of a drug solution container 110)" of the drug solution administration device 100, an arrow Y indicates a "width direction (depth direction)" of the drug solution administration device 100, and an arrow Z indicates a "height direction" of the drug solution administration device 100.

Drug Solution Administration System

The drug solution administration system 10 can be used to administer a drug solution into a living body. As illustrated in FIG. 1, the drug solution administration system 10 includes the drug solution administration device 100 and the administration instrument 200.

Figure 2:
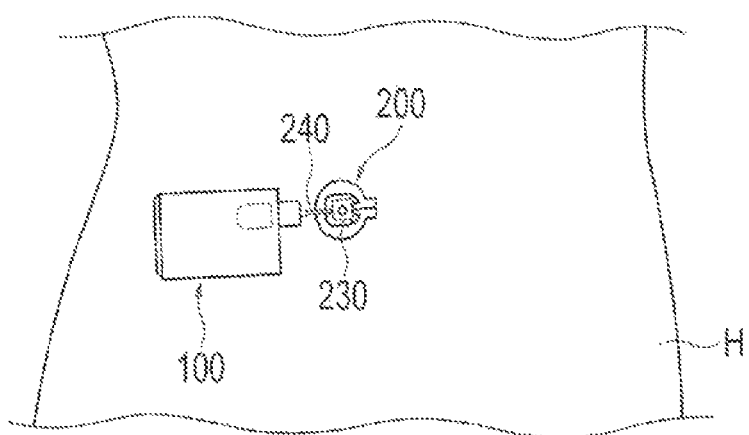
FIG. 2 is a view schematically illustrating a usage example of the drug solution administration system according to the present embodiment.

As illustrated in FIG. 2, the drug solution administration device 100 and the administration instrument 200 are constituted as a patch type to be used by being stuck to a body surface (skin) H of a user. A body part of the user to which the drug solution administration device 100 and the administration instrument 200 are to be attached is not particularly limited, and can be, for example, the abdomen or the thigh.

For example, the drug solution administration system 10 can continuously administer a drug solution filled in the drug solution container 110 included in the drug solution administration device 100 into a living body over a relatively long period (for example, about several minutes to several hours) by pressing action by a pusher 130 which will be described later. Note that the drug solution administration system 10 may intermittently administer the drug solution into the living body.

Drug Solution Administration Device

Figure 3:
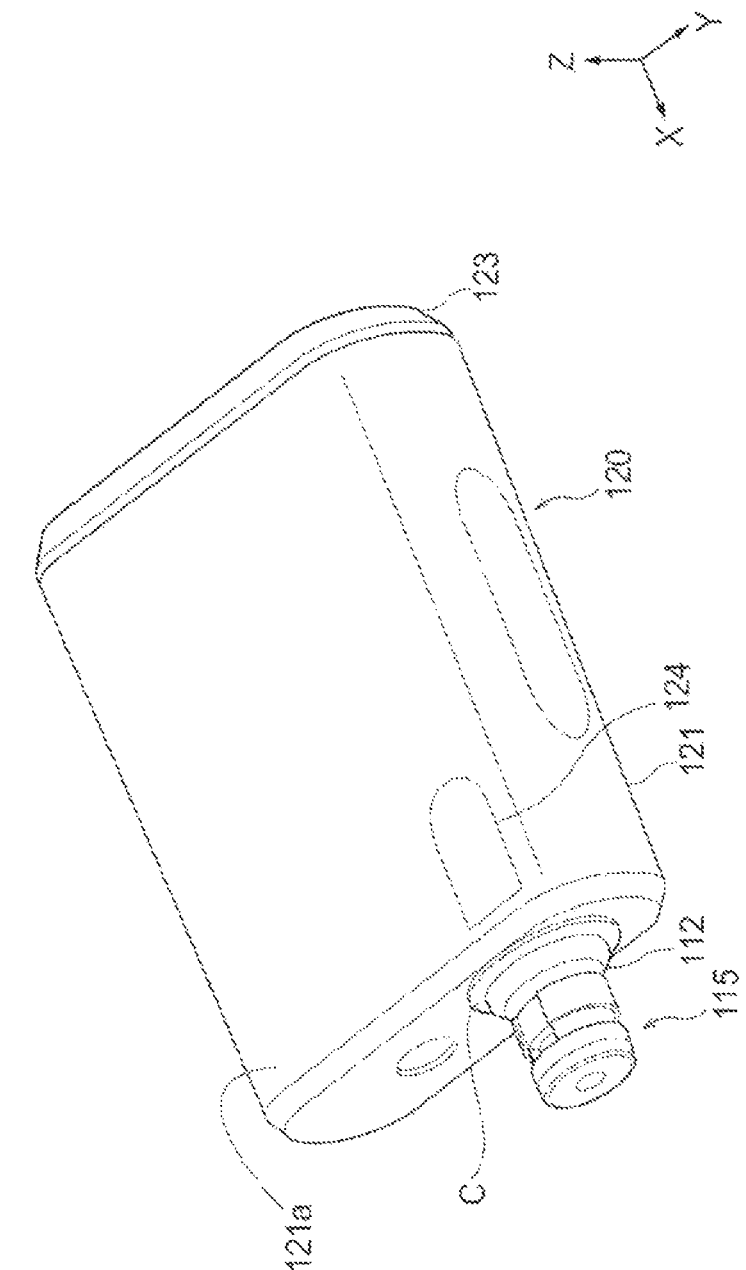
FIG. 3 is a schematic perspective view of a drug solution administration device constituting the drug solution administration system according to the present embodiment.
Figure 4:
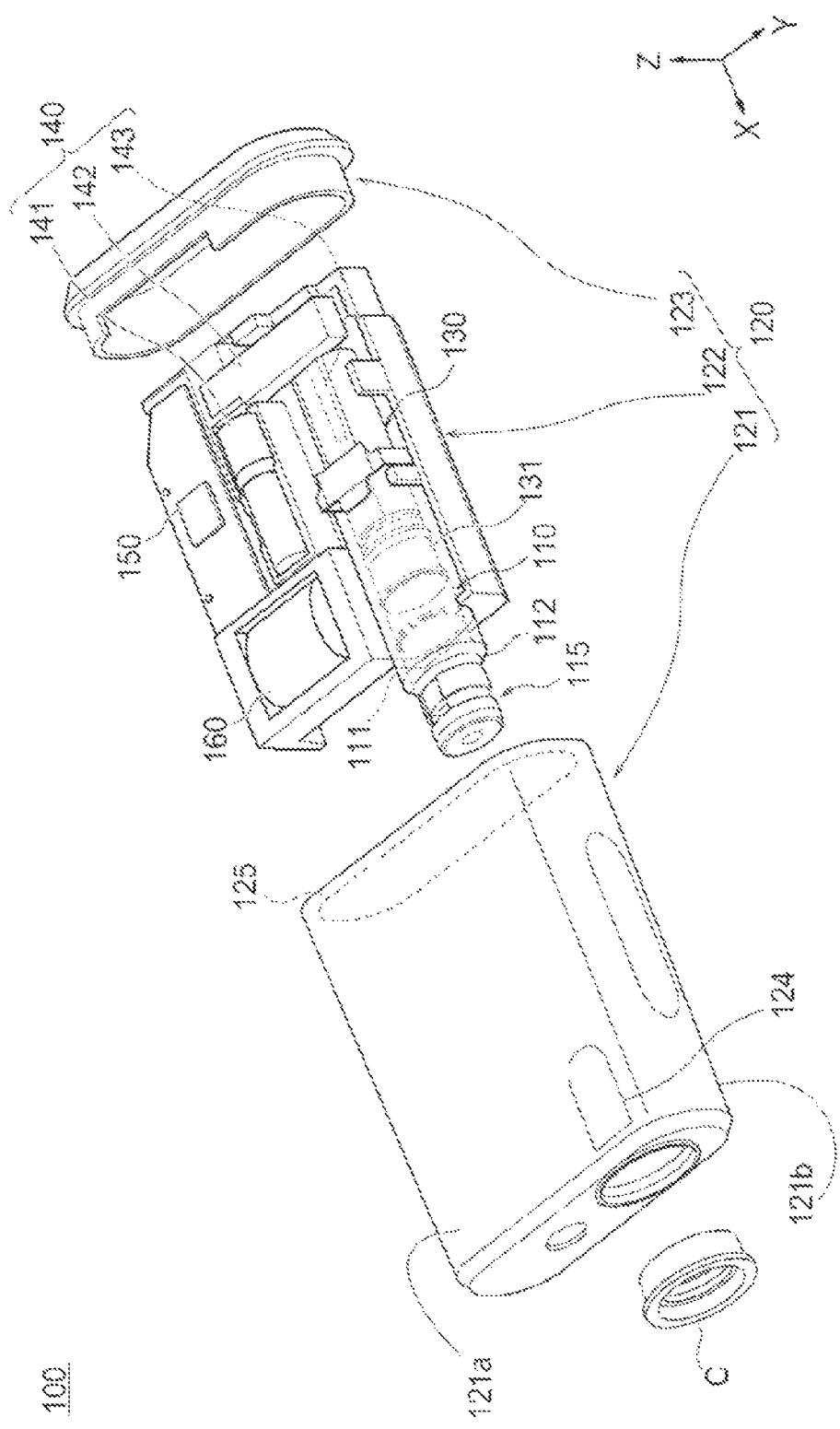
FIG. 4 is an exploded perspective view of the drug solution administration device according to the present embodiment.

As illustrated in FIGS. 3 and 4, the drug solution administration device 100 includes the drug solution container 110 filled with a drug solution, a housing 120 that holds the drug solution container 110, the pusher 130 that pushes out the drug solution within the drug solution container 110, a drive mechanism 140 that moves the pusher 130 forward and backward with respect to a distal end opening of the drug solution container 110, a control unit 150 that controls operation of the drive mechanism 140, and a power supply unit 160.

As illustrated in FIGS. 3 and 4, the housing 120 can include a box-shaped housing main body portion 121 in which a housing space is formed, a chassis 122 that is housed in the housing space of the housing main body portion 121 and can be fixed to the housing main body portion 121, and a lid member 123 that is attached to the housing main body portion 121 in a state where the chassis 122 is housed in the housing space.

Figure 5:
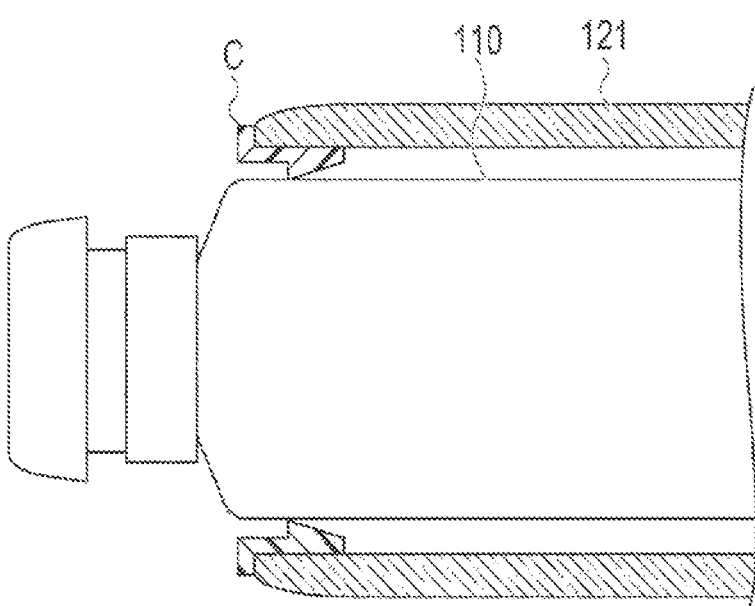
FIG. 5 is a partial cross-sectional view of a distal end side of the drug solution administration device according to the present embodiment.

As illustrated in FIGS. 3 to 5, a packing C is fitted in an opening of the housing main body portion 121. As illustrated in FIG. 5, the packing C is in linear contact with the drug solution container 110 in a circumferential direction. For convenience of description, FIG. 5 illustrates only a cross section of the housing main body portion 121 and the packing C.

As illustrated in FIGS. 3 and 4, a window portion 124 that allows inside of the housing space to be visually recognized from outside of the housing 120 is formed on the upper surface 121*a* of the housing main body portion 121. The window portion 124 is formed by providing a transparent or translucent portion in part of the housing main body portion 121.

As illustrated in FIG. 4, a proximal end opening 125 for inserting the chassis 122 into the housing space of the housing main body portion 121 is formed on a proximal end side in the longitudinal direction of the housing main body portion 121. As illustrated in FIGS. 3 and 4, the proximal end opening 125 of the housing main body portion 121 is closed by the lid member 123 in a state where the chassis 122 is housed in the housing space.

As illustrated in FIG. 4, a bottom surface 121*b* of the housing main body portion 121 can be provided with a sheet-like sticking portion that can be stuck to the body surface H of the user. In an initial state before the drug solution administration device 100 is attached to the user, a peelable protective sheet can be attached to a sticking surface of the sticking portion.

The chassis 122 holds the drug solution container 110, the pusher 130, the drive mechanism 140, the control unit 150, and the power supply unit 160.

The drug solution container 110 is a so-called prefilled drug solution container. Thus, a drug solution is filled in a lumen 111 of the drug solution container 110 in advance. Examples of the drug solution can include protein preparations, narcotic analgesics, diuretics, and the like.

A sealing member for preventing leakage of the drug solution is disposed in a distal end opening (discharge port) formed in the distal end portion 112 of the drug solution container 110. As illustrated in FIG. 3, the distal end portion 112 of the drug solution container 110 is disposed so as to protrude outward from the housing main body portion 121. In addition, a mounting portion 115 to be connected to a tube 240 (see FIG. 1) which will be described later is attached to the distal end portion of the drug solution container 110 protruding from the housing main body portion 121.

As illustrated in FIG. 4, the pusher 130 is inserted into the lumen 111 of the drug solution container 110. A gasket 131 slidable on an inner wall 110*a* (see FIGS. 8A and 8B) of the drug solution container 110 is disposed at a distal end of the pusher 130. The gasket 131 liquid-tightly seals a proximal end side of the gasket 131 by liquid-tightly bringing an outer peripheral portion of the gasket 131 into contact with an inner peripheral surface of the drug solution container 110. When the pusher 130 is caused to move forward in the longitudinal direction X and the distal end of the pusher 130 pushes the gasket 131, the gasket 131 can move forward, but there is no mechanical coupling between the pusher 130 and the gasket 131, and thus, when the pusher 130 is caused to move backward on the opposite side, the pusher 130 and the gasket 131 can be separated.

When the pusher 130 moves forward in a state where the gasket 131 is stopped in the drug solution container 110, the gasket 131 is compressed in a direction (longitudinal direction X) in which the pusher 130 moves forward. When the gasket 131 is compressed, a thickness in the longitudinal direction X decreases as compared with a thickness in the longitudinal direction X when the gasket 131 is not compressed. The state in which the gasket 131 is stopped in the drug solution container 110 means, for example, a state in which administration of the drug solution is completed and the gasket 131 is in contact (i.e., lies adjacent) with the inner wall 110*b* on the distal end side of the drug solution container 110 (see an upper part of FIG. 8A) or a state in which a supply route of the drug solution in the drug solution administration system 10 (administration instrument 200, or the like) is blocked and the gasket 131 is in contact with the drug solution retained in the drug solution container 110 (see an upper part of FIG. 8B). The gasket 131 can be formed with, for example, a flexible resin material such as a rubber material or an elastomer.

The drive mechanism 140 can include a motor 141 that receives a drive current from the power supply unit 160 and generates driving force for moving the pusher 130 forward and backward, and a speed reduction mechanism 142 including a gear, or the like, that transmits rotational driving force of the motor 141, a feed screw 143 connected to the speed reduction mechanism 142, and a rotation detection unit 144 that detects rotation of the motor 141.

The feed screw 143 converts rotational motion transmitted from the speed reduction mechanism 142 into linear motion to move the pusher 130 forward and backward in the longitudinal direction X.

The feed screw 143 is screwed in the vicinity of the proximal end of the pusher 130. The feed screw 143 converts rotational motion transmitted from the speed reduction mechanism 142 into linear motion to move the pusher 130 forward and backward in the longitudinal direction X. The pusher 130 causes the gasket 131 to move forward by moving forward toward the distal end side of the drug solution container 110 and pushes out the drug solution from the lumen 111 of the drug solution container 110 to the tube 240 (see FIG. 1).

Figure 6:
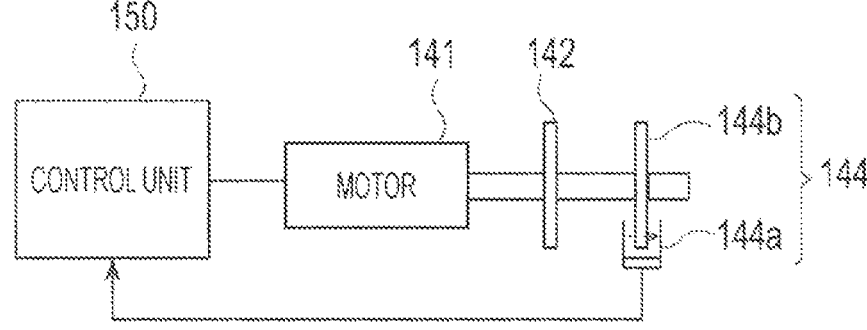
FIG. 6 is a block diagram of a control system of the drug solution administration device according to the present embodiment.
Figure 7:
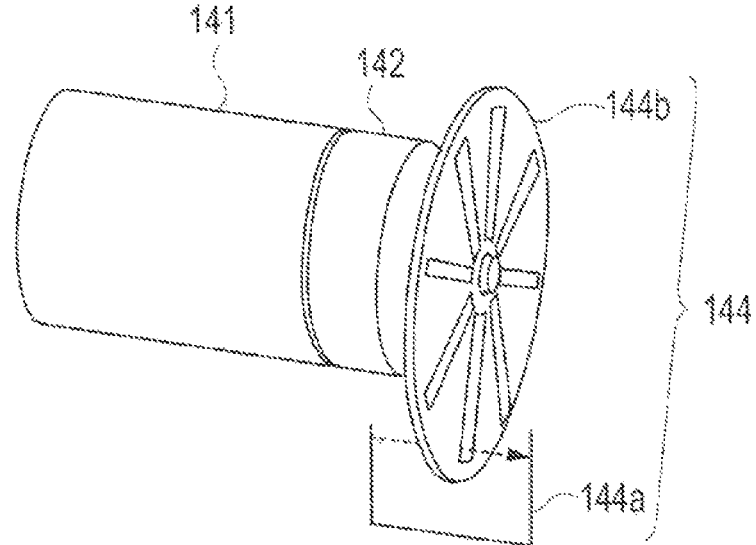

The rotation detection unit 144 can be an encoder provided at a distal end of the motor 141. As illustrated in FIGS. 6 and 7, the encoder includes a photointerrupter 144*a* including an optical sensor and a slit plate 144*b* in which a large number of slits are radially formed. The slit plate 144*b* rotates in association with rotation of the motor 141. The rotation detection unit 144 can detect rotation of the motor 141 by detecting whether or not light passes through the slits of the slit plate 144*b* with the optical sensor of the photointerrupter 144*a*. In the present embodiment, an encoder using the photointerrupter 144*a* is exemplified as the rotation detection unit 144, but an encoder using a magnetic sensor may be used. Furthermore, a position of the rotation detection unit 144 is not limited to the position illustrated in FIGS. 6 and 7, and rotation of the motor 141 may be directly detected by placing the rotation detection unit 144 between the motor 141 and the speed reduction mechanism 142.

The control unit 150 controls drug solution delivery operation of the drug solution administration device 100. The control unit 150 can be constituted with, for example, a microcomputer (electronic circuit element) on which a central processing unit (CPU), a random access memory (RAM), a read-only memory (ROM), and the like, are mounted. The control unit 150 integrally controls operation of the drive mechanism 140 and the power supply unit 160.

The power supply unit 160 can be constituted with, for example, a button battery, and the like.

The control unit 150 is electrically connected to the power supply unit 160, the motor 141, and the rotation detection unit 144. The motor 141 is rotated by power supplied from the power supply unit 160, and rotation speed of the motor 141 is controlled by the control unit 150 on the basis of the detection result of the rotation detection unit 144.

In the drug solution administration device 100, the control unit 150 causes the pusher 130 (gasket 131) to move forward in the drug solution container 110 to administer the drug solution to a living body. In this event, the control unit 150 rotates the motor 141 forward. On the other hand, when the gasket 131 stops against the pusher 130 that is about to move forward, the drug solution is not fed out from the drug solution container 110, and administration of the drug solution can be stopped. The control unit 150 can confirm that the motor 141 is stopped in association with stopping of the gasket 131 on the basis of the detection result of the rotation detection unit 144, and the like.

Figure 9:
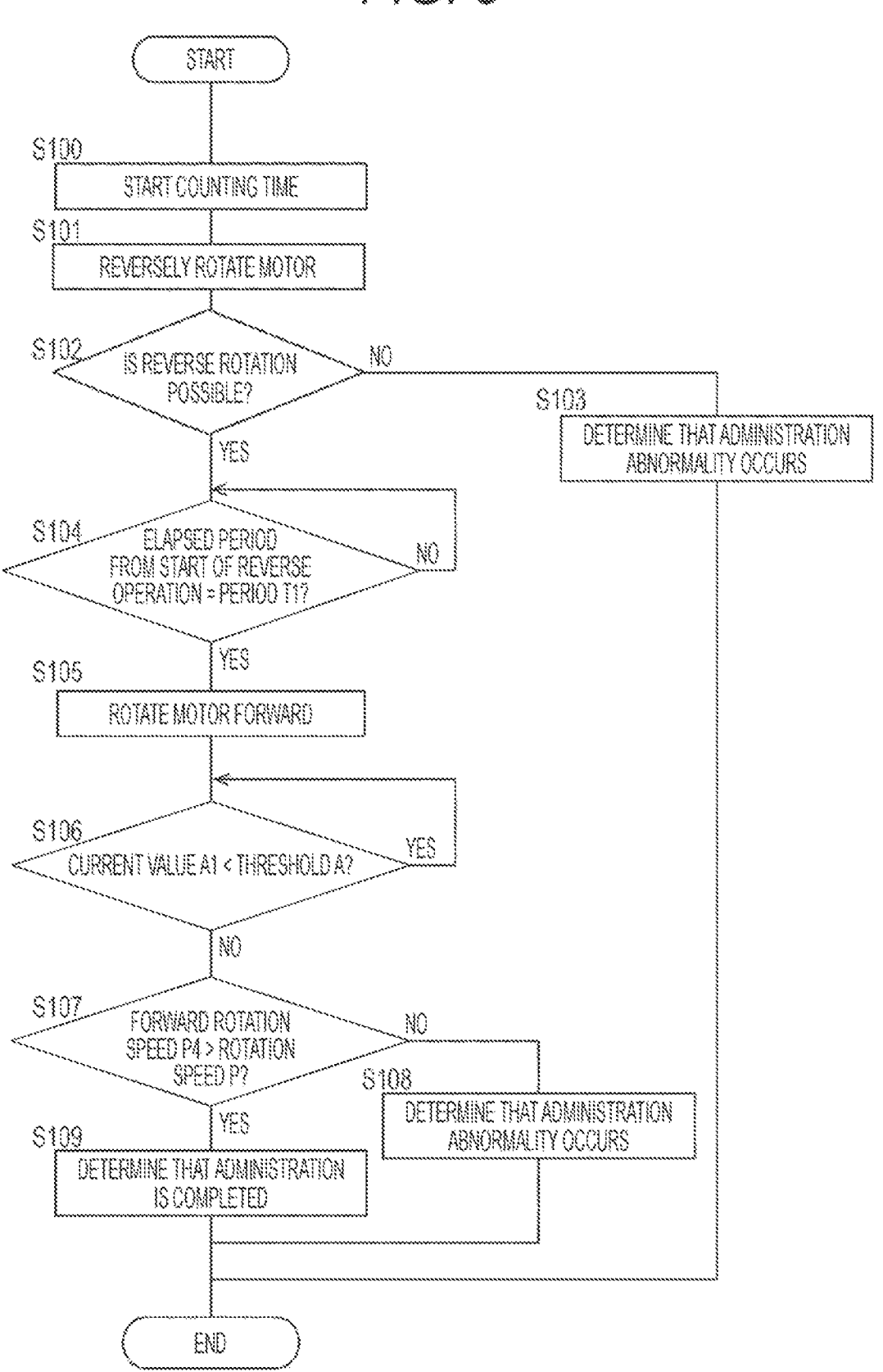
FIG. 9 is an operation flowchart of a control unit in the present embodiment.
Figure 10:
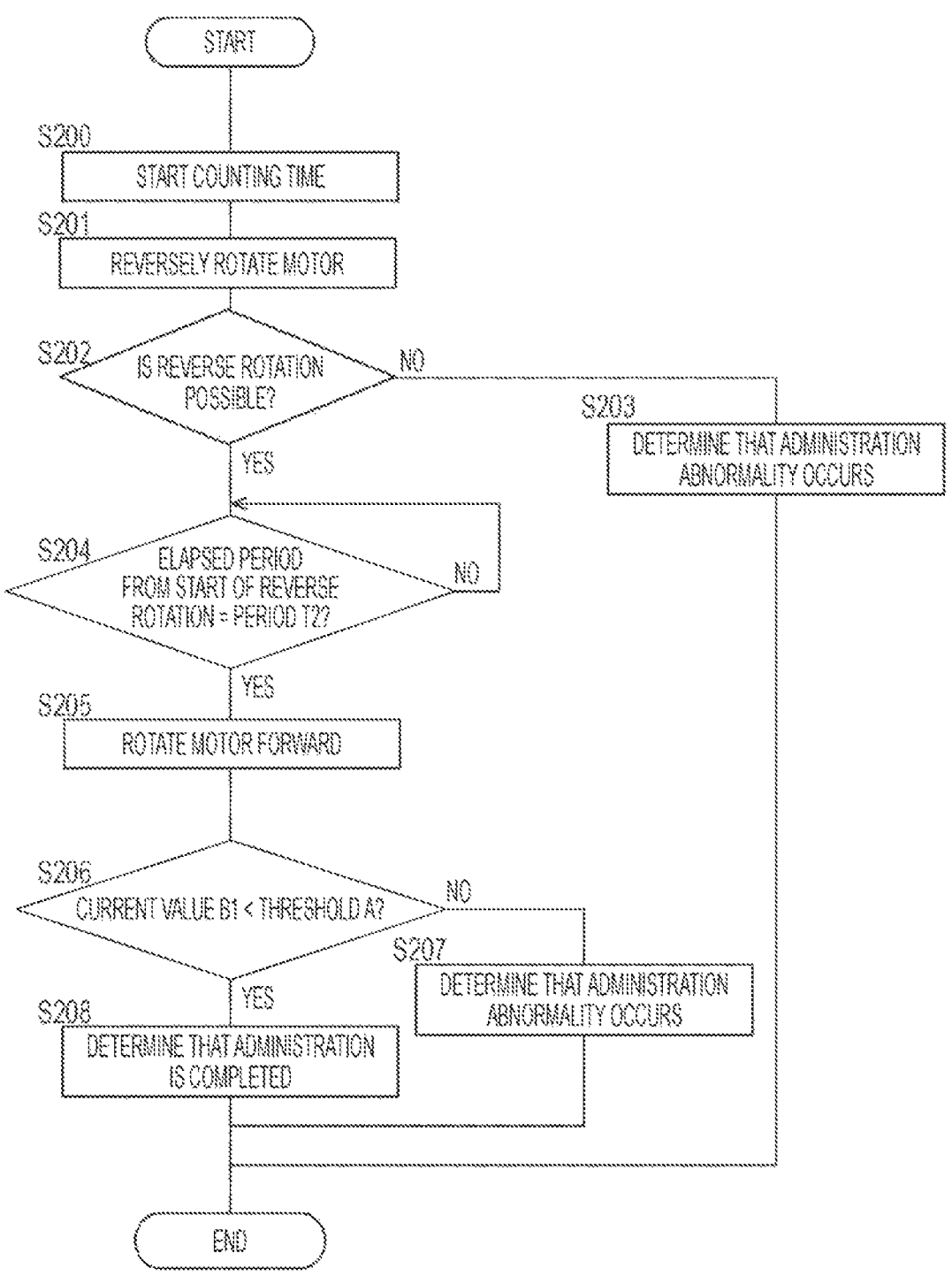
FIG. 10 is an operation flowchart of a control unit according to a second embodiment.

The drug solution administration device 100 can detect an administration condition of the drug solution with relatively higher accuracy by the control unit 150 performing confirmation operation illustrated in FIGS. 9 and 10 after confirming that the motor 141 is stopped. The confirmation operation of the control unit 150 will be described later.

Next, functions of the control unit 150 will be described.

The control unit 150 has an operation confirmation function of confirming an operating condition of the motor 141 on the basis of the detection result of the rotation detection unit 144. When the motor 141 is started (forward rotation or reverse rotation), the control unit 150 can determine that the motor 141 operates in a case where rotation (whether or not light passes) of the motor 141 is detected by the rotation detection unit 144. On the other hand, when the motor 141 is started (forward rotation or reverse rotation), the control unit 150 can determine that the motor 141 is stopped in a case where rotation of the motor 141 is not detected by the rotation detection unit 144. Note that in the present embodiment, the encoder using the photointerrupter 144*a* as the rotation detection unit 144 has been exemplified, but an encoder using a magnetic sensor may be used.

In addition, the control unit 150 can detect rotation number of the motor 141 by the operation confirmation function.

The control unit 150 has a rotation speed calculation function of calculating the rotation speed of the motor 141 on the basis of the detection result of the rotation detection unit 144. When administration of the drug solution is started, the control unit 150 can calculate the rotation speed of the motor 141 on the basis of an interval of the rotation of the motor 141 (whether or not light passes) detected by the rotation detection unit 144. The rotation speed of the motor 141 has a characteristic of decreasing as load increases (torque increases) and increasing as the load decreases in a case where a current flowing through the motor 141 is constant. In addition, the control unit 150 has a current value measurement function of measuring a current flowing through the motor 141. A value of the current flowing through the motor 141 has a characteristic of increasing as the load increases (torque increases) and decreasing as the load decreases in a case where the rotation speed of the motor 141 is constant.

With the rotation speed calculation function, the control unit 150 increases the current flowing through the motor 141 in a case where the rotation speed of the motor 141 decreases and decreases the current flowing through the motor 141 in a case where the rotation speed of the motor 141 increases, thereby maintaining the rotation speed of the motor 141 at preset speed (drug solution administration speed) while the drug solution is administered. On the other hand, in a case where administration of the drug solution is completed or an abnormality occurs in administration of the drug solution, even if the current flowing through the motor 141 is increased, the rotation speed of the motor 141 cannot be maintained at the drug solution administration speed and finally reaches a maximum value of the current that can flow through the motor 141, and the rotation speed of the motor 141 decreases. Thus, the control unit 150 can determine that the gasket 131 is stopped within the drug solution container 110 in a case where the rotation speed of the motor 141 falls below the drug solution administration speed by the rotation speed calculation function or in a case where the current value of the motor 141 reaches the maximum value by the current value measurement function. In order to determine rather early that the gasket 131 is stopped within the drug solution container 110, it may be determined that the gasket 131 is stopped within the drug solution container 110 in a case where the rotation speed of the motor 141 reaches a set value less than the drug solution administration speed by a predetermined amount or in a case where the current value of the motor 141 reaches a set value less than the maximum value by a predetermined value.

Administration Instrument

As illustrated in FIG. 1 and FIG. 2, the administration instrument 200 is constituted so as to be able to be connected to the drug solution administration device 100.

The administration instrument 200 can include a connector 210, a needle tube 220 that punctures the living body, a puncture unit (cannula housing) 230, a tube (i.e., tubular member) 240, and a puncture assist instrument 250 that assists puncture of the needle tube 220 into the living body.

The connector 210 is constituted so as to be able to be connected to the drug solution administration device 100 via a mounting portion 215 fixed to the connector 210. The mounting portion 215 can be connected to the drug solution administration device 100 by being externally fitted to the mounting portion 115 (see FIG. 4) provided at the distal end portion 112 of the drug solution container 110 protruding to outside of the housing 120.

Inside the mounting portion 215, a connection needle portion through which a sealing member disposed at the distal end portion 112 of the drug solution container 110 can be inserted is disposed. The tube 240 communicates with the lumen 111 of the drug solution container 110 via a needle portion for connection.

Inside the puncture unit 230, a flow path that communicates the tube 240 and the lumen of the needle tube 220 is formed. The drug solution fed to the puncture unit 230 through the tube 240 is administered into the living body through a flow path formed inside the puncture unit 230 and the needle tube 220.

To deliver the drug solution to the user, the puncture assist instrument 250 is attached to the puncture unit 230. The puncture assist instrument 250 holds an introduction needle (inner needle) 251. In a state where the puncture assist instrument 250 is attached to the puncture unit 230, the introduction needle 251 is inserted through the lumen of the needle tube 220, and a distal end of the introduction needle 251 protrudes from the distal end of the needle tube 220. By puncturing the living body with the needle tube 220 with the introduction needle 251 inserted into the needle tube 220, the user can insert the needle tube 220 into the living body while preventing the needle tube 220 from being broken, or the like.

The puncture assist instrument 250 is removed from the puncture unit 230 after puncturing the living body with the needle tube 220. When the puncture assist instrument 250 is removed from the puncture unit 230, the introduction needle 251 is removed from the lumen of the needle tube 220.

After puncturing the living body with the needle tube 220, the puncture assist instrument 250 is removed, and the puncture unit 230 is left on the body surface H of the user in a state where the needle tube 220 is indwelled in the living body. When the pusher 130 of the drug solution administration device 100 moves forward in the drug solution container 110 in this state, the drug solution filled in the drug solution container 110 is delivered to the lumen of the needle tube 220 via the tube 240 and the flow path of the puncture unit 230.

The introduction needle 251 can be formed with, for example, a metal needle. Further, the needle tube 220 can be formed with, for example, a resin tubular member (cannula).

In a similar manner to the drug solution administration device 100, the administration instrument 200 is constituted as a patch type to be used by being stuck to the body surface H of the user. A contact surface (bottom surface) 231 of the puncture unit 230 of the administration instrument 200 can be provided with a sheet-like sticking portion that can be stuck to the body surface H of the user. In an initial state before the administration instrument 200 is attached to the user, a peelable protective sheet is attached to the sticking surface of the sticking portion.

First Embodiment

Confirmation operation of the control unit 150 in the present embodiment will be described with reference to FIG. 9. FIG. 9 is an operation flowchart of the control unit 150 in the present embodiment.

As described above, the confirmation operation of the control unit 150 is performed after administration of the drug solution is started and the control unit 150 confirms that the motor 141 is stopped by the operation confirmation function (administration of the drug solution is stopped). In this event, the control unit 150 may stop start of the motor 141 after confirming that the motor 141 is stopped.

First, the control unit 150 sets first rotation number and second rotation number of the motor 141 corresponding to push return amounts L1 and L2 of the gasket 131.

Push Return Amount L1

Figure 8A:
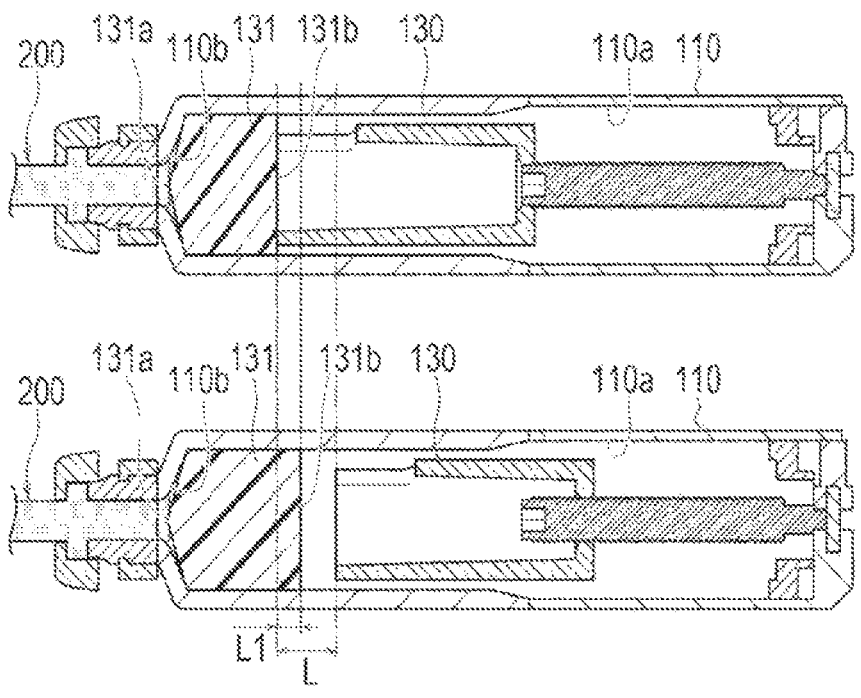
FIG. 8A is a cross-sectional view of the drug solution administration device illustrating a state where a pusher is stopped and a state where the pusher is caused to move backward when administration is completed.

In a case where administration of the drug solution is completed, the gasket 131 is stopped in a state of being in contact with the inner wall 110b on the distal end side of the drug solution container 110 as illustrated in the upper part of FIG. 8A. When the gasket 131 is released from pressing by the pusher 130 due to backward movement of the pusher 130, a thickness of the gasket increases from a compression state in which the thickness decreases by pressing and returns to the original uncompressed state. Thus, when the gasket 131 is released from pressing by the pusher 130, a position of the proximal end portion 131b is moved closer to the proximal end side without changing the position of the distal end portion 131a (see the lower part of FIG. 8A). In the present specification, when the gasket 131 is released from pressing by the pusher 130, an increase amount in the thickness of the gasket 131 caused by the gasket 131 returning from the compressed state to the uncompressed state will be referred to as a push return amount L1.

Push Return Amount L2

Figure 8B:
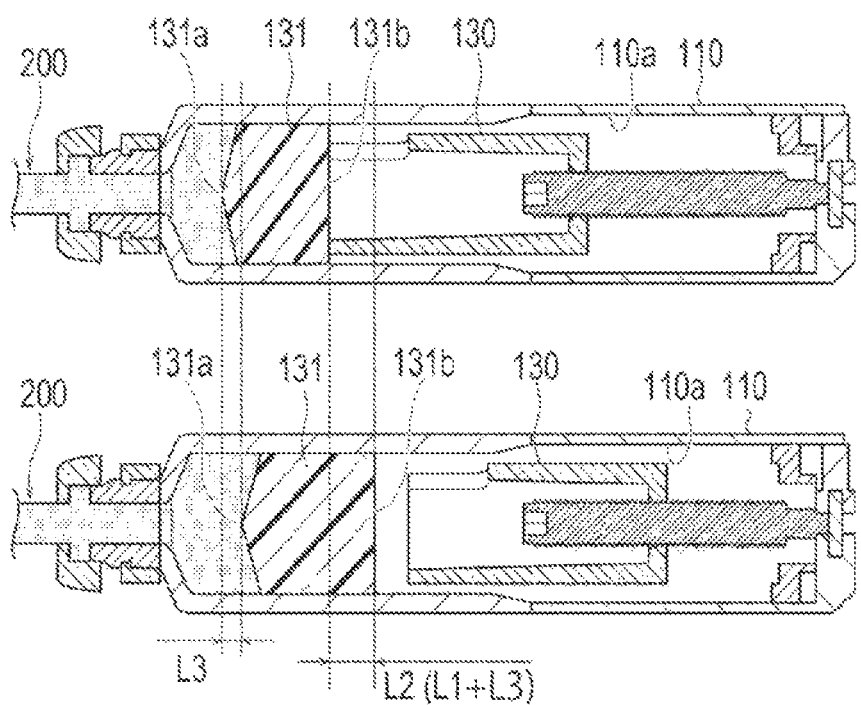
FIG. 8B is a cross-sectional view of the drug solution administration device illustrating a state where the pusher is stopped and a state where the pusher is caused to move backward when an administration abnormality occurs (when a supply route is blocked).

When the supply route is blocked (administration abnormality occurs), the gasket 131 is stopped in a state of being in contact with the drug solution retained on the distal end side of the drug solution container 110 as illustrated in the upper part of FIG. 8B. In this event, the gasket 131 is in a compressed state, and a pressure applied to the drug solution container 110 and the drug solution retained in the supply route is higher than a pressure on the proximal end portion 131*b* side of the gasket 131. When the gasket 131 is released from pressing of the pusher 130 by backward movement of the pusher 130, the thickness of the gasket 131 increases by the state of the gasket returning from the compressed state to the uncompressed state, and the increased pressure applied to the drug solution container 110 and the drug solution retained in the supply route moves the gasket 131 to the proximal end side (see the lower part of FIG. 8B). In the present specification, an amount of increase in the thickness of the gasket 131 caused by the state of the gasket 131 returning from the compressed state to the uncompressed state when the gasket 131 is released from pressing by the pusher 130 will be referred to as a push return amount L1 in a case where administration of the drug solution is completed. In addition, an amount of movement of the gasket 131 due to the increased pressure applied to the drug solution container 110 and the drug solution retained in the supply route will be referred to as a push return amount L3. Further, a sum of the push return amount L1 and the push return amount L3 will be referred to as a push return amount L2.

Note that values of the push return amounts L1 and L2 of the gasket 131 may be set in advance. Further, values of the first rotation number and the second rotation number of the motor 141 may be set in advance.

Then, the control unit 150 starts counting time (S100) and starts reverse rotation of the motor 141 at preset speed (pusher reverse speed) on the basis of an operating period of the motor 141 or third rotation number set in accordance with the return amount L of the pusher 130 (see FIG. 8A) (S101). In this event, the control unit 150 sets the return amount L of the pusher 130.

The return amount L of the pusher 130 is a distance by which the motor 141 is reversely rotated to move the pusher 130 from a current position to the proximal end side and can be set in consideration of the push return amounts L1 and L2 of the gasket 131.

The return amount L of the pusher 130 in the present embodiment is set to a value greater than the push return amount L2 of the gasket 131.

The proximal end portion 131*b* of the gasket 131 does not move from a stop position to the proximal end side by the push return amount L2 when released from pressing by the pusher 130 regardless of whether administration is completed or an abnormality occurs in the administration. Thus, in a case where the return amount L is set to a value greater than the push return amount L2, the control unit 150 can cause the distal end portion of the pusher 130 to move farther backward from the position of the proximal end portion 131*b* of the pushed back gasket 131 to the proximal end side.

The return amount L of the pusher 130 and the value of the operating period or the third rotation number of the motor 141 corresponding to the return amount L of the pusher 130 may be set in advance. The operating period of the motor 141 corresponding to the return amount L of the pusher 130 means a period required for the pusher 130 to move by the return amount L at the pusher reverse speed. The third rotation number of the motor 141 corresponding to the return amount L of the pusher 130 means rotation number of the motor 141 required to move the pusher 130 by the return amount L. Note that in a case where the pusher reverse speed cannot be set faster than speed at which the proximal end portion 131*b* of the gasket 131 moves, there is a possibility that the proximal end portion 131*b* of the gasket 131 comes into contact with the pusher 130, and the operating period of the motor 141 corresponding to the return amount L of the pusher 130 cannot be accurately measured, and thus, the third rotation number corresponding to the return amount L of the pusher 130 is used.

Then, the control unit 150 starts reverse rotation of the motor 141 and determines whether or not the pusher 130 moves backward by the operation confirmation function of confirming the operating condition of the motor 141 on the basis of the detection result of the rotation detection unit 144 (S102).

In a case where the pusher 130 does not move backward (the motor 141 does not operate) (S102: No), the control unit 150 determines that a failure occurs in the motor 141. Then, the control unit 150 determines that an administration abnormality of the drug solution occurs due to the failure of the motor 141 (S103). In a case where the pusher 130 does not move backward, it is suspected that a failure occurs in the motor 141 and/or the speed reduction mechanism 142. However, in the following description, it is assumed that a failure occurs in the motor 141.

On the other hand, in a case where the pusher 130 moves backward (the motor 141 operates) (S102: Yes), the control unit 150 determines that an administration abnormality occurs due to a factor other than the failure of the motor 141 or administration of the drug solution is completed.

As described above, after confirming that the motor 141 is stopped, the control unit 150 can confirm the operating condition of the motor 141 by starting reverse rotation of the motor 141 to determine whether or not the pusher 130 moves backward (step S102) and can determine whether or not an administration abnormality of the drug solution occurs due to the failure of the motor 141. As a result, the drug solution administration device 100 can detect the administration condition of the drug solution with relatively higher accuracy.

Then, in a case where the motor 141 operates (S102: Yes), the control unit 150 determines whether or not a period T1 (corresponding to the "predetermined period") has elapsed since start of reverse rotation of the motor 141 (S104).

The period T1 is set longer than the longer one of a period required for the proximal end portion 131*b* of the gasket 131 released from pressing by the pusher 130 to finish moving by the push return amount L1 and a period required for the proximal end portion 131*b* to finish moving by the push return amount L2. Note that a value of the period T1 may be set within the confirmation operation or may be set in advance.

Then, in a case where the period T1 has not elapsed since start of the reverse rotation of the motor 141 (S104: No), the control unit 150 repeats step S104.

On the other hand, in a case where the period T1 has elapsed from the reverse rotation of the motor 141 (S104: Yes), the control unit 150 rotates the motor 141 forward (S105). In this event, the control unit 150 uses the rotation speed calculation function to rotate the motor 141 at preset speed (pusher forward speed). In addition, the control unit 150 measures fourth rotation number (P4 illustrated in FIG. 9, hereinafter referred to as rotation number P4) of the motor 141 and a current value A1 while the motor 141 rotates forward by the operation confirmation function and the current value measurement function.

Then, the control unit 150 determines whether or not the current value A1 of the motor 141 measured by the current value measurement function is less than a threshold A (S106). The threshold A is an upper limit current value for the pusher 130 to move forward in an unloaded state (a state where the pusher 130 is not in contact with the gasket 131). When the pusher 130 is in contact with the gasket 131 while the motor 141 is rotating at the pusher forward speed in an unloaded state of the pusher 130, the load of the motor 141 increases, and the current flowing through the motor 141 to maintain the pusher forward speed becomes higher than the upper limit current.

In a case where the current value A1 of the motor 141 is less than the threshold A (S106: Yes), the control unit 150 determines that the pusher 130 is not in contact with the gasket 131 (the gasket 131 is stopped in front of the position of the pusher 130) and repeats step S106 to cause the pusher 130 to move further forward.

On the other hand, in a case where the current value A1 of the motor 141 is equal to the threshold A or greater than the threshold A (S106: No), the control unit 150 determines that the distal end portion of the pusher 130 is in contact with the proximal end portion 131b of the gasket 131 and stops the pusher 130 (stops operation of the motor 141), and the processing proceeds to step S107.

Then, when the current value A1 measured by the current value measurement function exceeds the threshold A (S106: No), the control unit 150 determines whether or not rotation number P4 measured by the operation confirmation function is higher than the rotation number P (S107). Note that the determination in step S106 may be made based on the rotation speed of the motor 141, and the control unit 150 may determine whether or not the rotation number P4 measured by the operation confirmation function is greater than the rotation number P when the measured rotation speed becomes less than a predetermined rotation speed (threshold) for determining that that the distal end portion of the pusher 130 is in contact with the proximal end portion 131b of the gasket 131. The rotation number P4 is a value of the rotation number of the motor 141 since start of the forward rotation of the motor 141 in step S105 to stop of the operation of the motor 141 as a result of a negative determination result being obtained in step S106, and the rotation number P is a value obtained by subtracting the first rotation number from the third rotation number. Here, the third rotation number refers to the rotation number of the motor 141 corresponding to the return amount L of the pusher 130 and refers to the rotation number of the motor 141 necessary to move the pusher 130 by the return amount L. The first rotation number refers to the rotation number of the motor 141 corresponding to the push return amount L1 of the gasket 131 and refers to the rotation number of the motor 141 necessary to move the pusher 130 by the push return amount L1.

In a case where the rotation number P4 of the motor 141 is equal to the rotation number P or lower than the rotation number P (S107: No), the control unit 150 determines that an amount of movement of the gasket 131 when released from pressing by the pusher 130 is equal to or greater than the push return amount L1. Thus, the control unit 150 determines that the gasket 131 is pushed back by a distance equal to or greater than a distance when the state returns from the compressed state to the uncompressed state and determines that an administration abnormality of the drug solution occurs due to blockage of the supply route (S108). In addition, the control unit 150 can determine a position of the gasket 131 that is in contact with the pusher 130 from the rotation number P4 of the motor 141 and can predict a degree of blockage of the supply route.

On the other hand, in a case where the rotation number P4 of the motor 141 is higher than the rotation number P (S107:

Yes), the control unit 150 determines that the amount of movement of the gasket 131 when released from pressing by the pusher 130 is less than the push return amount L1. Thus, the control unit 150 determines that the gasket 131 is not pushed back by a distance equal to or longer than a distance when the state returns from the compressed state to the uncompressed state and determines that administration of the drug solution is completed (S109).

Note that the drug solution administration device 100 may include a notification unit that gives a notification of detection of an administration abnormality of the drug solution. The notification unit can be, for example, an LED provided in the housing 120 of the drug solution administration device 100. The notification unit can give a notification of an administration abnormality of the drug solution by turning on and blinking the LED. Note that the notification unit may be a speaker provided in the housing 120 of the drug solution administration device 100, and the control unit 150 may make a notification of an administration abnormality of the drug solution by sounding the speaker. In addition, the notification unit may wirelessly notify an external portable terminal or computer of an administration abnormality of the drug solution.

As described above, the drug solution administration device 100 according to the present embodiment includes a pusher 130 configured to push a drug solution in a drug solution container 110 filled with the drug solution, a drive mechanism 140 configured to move the pusher 130 forward and backward with respect to a distal end opening of the drug solution container 110, and a control unit 150 configured to control operation of the drive mechanism 140, the drive mechanism 140 includes a motor 141 configured to generate driving force for moving the pusher 130 forward and backward, and a rotation detection unit 144 configured to detect rotation of the motor 141, the control unit 150 has an operation confirmation function of confirming an operating condition of the motor 141 on the basis of a detection result of the rotation detection unit 144, and after confirming that the motor 141 is stopped by the operation confirmation function, the control unit 150 starts reverse rotation of the motor 141 to determine whether or not the pusher 130 moves backward.

According to the drug solution administration device 100, after confirming that the motor 141 is stopped, the control unit 150 can confirm the operating condition of the motor 141 and can determine whether or not an administration abnormality of the drug solution occurs due to a failure of the motor 141 by starting the reverse rotation of the motor 141 to determine whether or not the pusher 130 moves backward. As a result, the drug solution administration device 100 can detect the administration condition of the drug solution with relatively higher accuracy.

In addition, the drug solution administration device 100 includes a gasket 131 slidable on the inner wall 110a of the drug solution container 110 and separated from the pusher 130, and a distal end of the pusher 130 pushes the gasket 131 to push the drug solution from within the drug solution container 110. With such a configuration, the gasket 131 is separated from the pusher 130 when the pusher 130 is caused to move backward.

Further, the control unit 150 determines whether or not the pusher 130 is in contact with the gasket 131 by rotating the motor 141 forward after causing the pusher 130 to move backward by reverse rotation of the motor 141. With this configuration, the drug solution administration device 100 can detect the administration condition of the drug solution with relatively higher accuracy.

Further, the drug solution administration device 100 is a drug solution administration device including a drug solution container 110 filled with a drug solution, a gasket 131 slidable on an inner wall 110a within the drug solution container 110, a pusher 130 configured to push the gasket 131, a drive mechanism 140 configured to cause the pusher 130 to move forward and backward with respect to a distal end opening of the drug solution container 110, and a control unit 150 configured to control operation of the drive mechanism 140, the drive mechanism 140 includes a motor 141 configured to generate driving force for moving the pusher 130 forward and backward, and a rotation detection unit 144 configured to detect rotation of the motor 141, the control unit 150 has an operation confirmation function of confirming an operating condition of the motor 141 on the basis of a detection result of the rotation detection unit 144, and the control unit 150 determines whether or not the pusher 130 is in contact with the gasket 131 by causing the motor 141 to perform reverse rotation to move the pusher 130 backward and subsequently causing the motor 141 to rotate forward after confirming that the motor 141 is stopped by the operation confirmation function. With this configuration, the drug solution administration device 100 can detect the administration condition of the drug solution with relatively higher accuracy.

Further, the control unit 150 determines whether or not the pusher 130 lies adjacent or is in contact with the gasket 131 based the current value A1 flowing through the motor 141 or the rotation speed of the motor 141. In a case where the determination is made on the basis of the current value A1 flowing through the motor 141, the control unit 150 can determine whether the current value falls below an upper limit current value (threshold A) for the pusher 130 to move forward in an unloaded state (state where the pusher 130 is not in contact with the gasket 131). In a case where the determination is made on the basis of the rotation speed of the motor 141, the control unit 150 can determine whether the measured rotation speed falls below predetermined rotation speed for determining whether or not the pusher 130 is in contact with the gasket 131. As a result, the drug solution administration device 100 can detect the administration condition of the drug solution with relatively higher accuracy.

In addition, the control unit 150 determines whether administration of the drug solution within the drug solution container 110 is completed or whether blockage occurs depending on whether or not the pusher 130 is in contact with the gasket 131. As a result, the drug solution administration device 100 can detect the administration condition of the drug solution with relatively higher accuracy.

Furthermore, the control unit 150 causes the motor 141 to rotate forward after waiting for a lapse of a period T1 (predetermined period) or more after the motor 141 is reversely rotated. As a result, the drug solution administration device 100 can detect the administration condition of the drug solution with relatively higher accuracy.

The period T1 (predetermined period) is a period from when the motor 141 is reversely rotated to when movement of the gasket 131 is stopped. As a result, the drug solution administration device 100 can detect the administration condition of the drug solution with relatively higher accuracy.

Further, when the pusher does not move backward even if the motor is reversely rotated, it is determined that a failure occurs in the motor. As a result, the drug solution administration device 100 can detect the administration condition of the drug solution with relatively higher accuracy.

Second Embodiment

Next, confirmation operation of the control unit 150 in a second embodiment will be described with reference to FIG. 10. FIG. 10 is an operation flowchart of the control unit 150 according to the second embodiment.

First, the control unit 150 sets first rotation number and second rotation number of the motor 141 corresponding to push return amounts L1 and L2 of the gasket 131. Values of the push return amounts L1 and L2, or values of the first rotation number and the second rotation number may be set in advance.

The control unit 150 starts counting time (S200) and starts reverse rotation of the motor 141 at preset pusher reverse speed on the basis of the operating period or the fifth rotation number of the motor 141 set in accordance with a second return amount of the pusher 130 so that the position of the pusher 130 moves to the proximal end side by the second return amount from the current stop position (S201). In this event, the control unit 150 sets the second return amount of the pusher 130.

The second return amount of the pusher 130 is set to a value greater than the push return amount L1 and less than the push return amount L2 of the gasket 131. Thus, in a case where the supply route is blocked, an amount by which the gasket 131 is pushed back is greater than the second return amount of the pusher 130, and in a case where administration of the drug solution is completed, the amount by which the gasket 131 is pushed back is less than the second return amount of the pusher 130.

The second return amount of the pusher 130 and the value of the operating period or the fifth rotation number of the motor 141 corresponding to the second return amount of the pusher 130 may be set in advance. The operating period of the motor 141 corresponding to the second return amount of the pusher 130 means a period required for the pusher 130 to move by the second return amount at the pusher reverse speed. The fifth rotation number of the motor 141 corresponding to the second return amount of the pusher 130 means rotation number of the motor 141 required for the pusher 130 to move by the second return amount. In a case where the pusher reverse speed cannot be set faster than speed at which the proximal end portion 131b of the gasket 131 moves, the proximal end portion 131b of the gasket 131 and the pusher 130 may come into contact with each other, and the operating period of the motor 141 corresponding to the second return amount of the pusher 130 cannot be accurately measured, and thus, the fifth rotation number corresponding to the second return amount of the pusher 130 is used.

Then, the control unit 150 starts reverse rotation of the motor 141 and determines whether or not the pusher 130 moves backward by the operation confirmation function of confirming the operating condition of the motor 141 on the basis of the detection result of the rotation detection unit 144 (S202).

In a case where the pusher 130 does not move backward (the motor 141 does not operate) (S202: No), the control unit 150 determines that a failure occurs in the motor 141. Then, the control unit 150 determines that an administration abnormality of the drug solution occurs due to the failure of the motor 141 (S203).

On the other hand, in a case where the motor 141 operates (S202: Yes), the control unit 150 determines that an administration abnormality occurs due to a factor other than the failure of the motor 141 or that administration of the drug solution is completed.

As described above, after confirming that the motor 141 is stopped, the control unit 150 can confirm the operating condition of the motor 141 and can determine whether or not an administration abnormality of the drug solution occurs due to a failure of the motor 141 by starting reverse rotation of the motor 141 to determine whether or not the pusher 130 moves backward (step S202).

Then, in a case where the motor 141 operates (S202: Yes), the control unit 150 determines whether or not a period T2 (corresponding to the "predetermined period") has elapsed since start of the reverse rotation of the motor 141 (S204).

The period T2 is set to be longer than (i.e., greater than) the longer one of a period required for the proximal end portion 131*b* of the gasket 131 released from pressing by the pusher 130 to finish moving by the push return amount L1 or a period required for the proximal end portion 131*b* to finish moving by the push return amount L2. Note that a value of the period T2 may be set in the confirmation operation or may be set in advance.

Then, in a case where the period T2 has not elapsed since start of the reverse rotation of the motor 141 (S204: No), the control unit 150 repeats step S204.

On the other hand, in a case where the period T2 has elapsed since the reverse rotation of the motor 141 (S204: Yes), the control unit 150 rotates the motor 141 forward (S205). In this event, the control unit 150 uses the rotation speed calculation function to rotate the motor 141 at preset speed. Note that the second return amount of the pusher 130 is set to a value greater than the push return amount L1 and less than the push return amount L2, and the period T2 is set to be greater than the longer one of a period required for the proximal end portion 131*b* of the gasket 131 released from pressing by the pusher 130 to finish moving by the push return amount L1 or a period required for the proximal end portion 131*b* to finish moving by the push return amount L2, and thus, in a case where the supply route is blocked, the proximal end portion 131*b* of the gasket 131 is in contact with the distal end side of the pusher 130 at a time point at which the period T2 elapses since the reverse operation of the motor 141, and in a case where administration is completed, the proximal end portion 131*b* of the gasket 131 is not in contact with the distal end side of the pusher 130. In addition, the control unit 150 measures a current value B1 immediately after the motor 141 is rotated forward using the current value measurement function.

Then, the control unit 150 determines whether or not the current value B1 of the motor 141 is less than the threshold A (S206). Note that the rotation speed of the motor 141 may be measured, and the determination may be made on the basis of whether or not the rotation speed is less than a predetermined rotation speed (threshold) for determining whether or not the pusher 130 is in contact with the gasket 131.

In a case where the current value B1 of the motor 141 (the current value immediately after the forward rotation of the motor 141) is equal to the threshold A or greater than the threshold A (S206: No), the control unit 150 determines that the pusher 130 is in contact with the gasket 131. Thus, the control unit 150 determines that an amount of movement (distance) of the gasket 131 when released from pressing by the pusher 130 is equal to the second return amount. Then, the control unit 150 determines that the gasket 131 is pushed back by a distance equal to or greater than the distance when the state returns from the compressed state to the uncompressed state and determines that an administration abnormality of the drug solution occurs due to blockage of the supply route (S207).

On the other hand, the control unit 150 determines that the pusher 130 stopped within the drug solution container 110 is not in contact with the gasket 131 in a case where the current value B1 of the motor 141 (the current value B1 of the motor 141 immediately after the forward rotation) is less than the threshold A (S206: Yes). Thus, the control unit 150 determines that the amount of movement (distance) of the gasket 131 when released from pressing by the pusher 130 is less than the second return amount. Then, the control unit 150 determines that the gasket 131 is not pushed back by a distance equal to or longer than (i.e., greater than) a distance when the state returns from the compressed state to the uncompressed state and determines that administration of the drug solution is completed (S208).

As described above, the control unit 150 according to the second embodiment has a current value measurement function for measuring a current value flowing through the motor 141, the control unit 150 sets the second return amount for causing the pusher 130 to move backward after confirming that the motor 141 is stopped, the operating period of the motor 141 corresponding to the second return amount, and the period T2 (predetermined period) set to be longer than the operating period of the motor 141, and the control unit 150 rotates the motor 141 forward after the period T2 has elapsed since the reverse rotation of the motor 141, and immediately after the motor 141 is rotated forward, determines whether the current value B1 measured by the current value measurement function falls below the threshold A (upper limit current value set in advance), or, alternatively, whether or not the rotation speed measured by the encoder is less than a threshold (predetermined upper limit rotation speed). As a result, the control unit 150 can determine whether or not the pusher 130 is in contact with the gasket 131 and can determine whether or not an administration abnormality of the drug solution occurs due to blockage of the supply route.

Further, the gasket 131 disposed at the distal end of the pusher 130 and slidable on the inner wall of the drug solution container 110 is provided, and the second return amount is set to a value greater than the push return amount L1 and less than the push return amount L2. Thus, in a case where the supply route is blocked, the gasket 131 is in contact with the distal end side of the pusher 130 before forward movement following backward movement of the pusher 130. Thus, the control unit 150 can determine whether or not an administration abnormality of the drug solution occurs due to blockage of the supply route by determining whether or not the current value B1 of the motor 141 falls below the threshold A. In addition, by setting the second return amount of the pusher 130 to a value less than the push return amount L2, protrusion of the pusher 130 from the drug solution container 110 due to backward movement of the pusher 130 is reduced, so that a size of the drug solution administration device 100 can be further reduced.

Note that there is a case where the push return amount (L1 illustrated in FIG. 8B) based on the increase in the thickness of the gasket 131 from the compressed state to the uncompressed state in a case where the supply route is blocked does not match the push return amount L1 (see FIG. 8A) in a case where administration of the drug solution is completed depending on viscosity of the drug solution being used or a material of the gasket 131, in which case, the push return amount based on the increase in the thickness of the gasket 131 from the compressed state to the uncompressed state in a case where the supply route is blocked may be separately set, and an amount obtained by combining the push return amount L3 and the separately set push return amount may be set as the push return amount L2.

Although the drug solution administration device according to the present disclosure has been described above through the embodiments, the present disclosure is not limited to each of the described configurations and can be appropriately changed on the basis of the description of the claims.

The detailed description above describes embodiments of a drug solution administration device. These disclosed embodiments represent examples of the drug solution administration device disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A drug solution administration device comprising:
a pusher configured to push a drug solution in a drug solution container filled with the drug solution;
a drive mechanism configured to move the pusher forward and backward with respect to a distal end opening of the drug solution container;
a microcomputer configured to control operation of the drive mechanism,
wherein the drive mechanism includes a motor configured to generate a driving force for moving the pusher forward and backward, and an encoder configured to detect rotation of the motor,
the microcomputer has an operation confirmation function of confirming an operating condition of the motor based on a detection result of the encoder, and
the microcomputer is configured to start a reverse rotation of the motor to determine whether or not the pusher moves backward after confirming that the motor is stopped by the operation confirmation function;
a gasket configured to be slidable on an inner wall of the drug solution container and separable from the pusher, wherein a distal end of the pusher is configured to push the gasket to push the drug solution from within the drug solution container toward the distal end opening of the drug solution container; and
wherein the microcomputer is configured to determine whether or not the pusher is in contact with the gasket by rotating the motor forward after causing the pusher to move backward by reverse rotation of the motor.

2. The drug solution administration device according to claim 1, wherein the microcomputer is configured to determine whether or not the pusher is against the gasket based on a value of a current flowing through the motor or rotation speed of the motor.

3. The drug solution administration device according to claim 1, wherein the microcomputer is configured to determine whether administration of the drug solution within the drug solution container is completed or a blockage occurs, based on whether or not the pusher is against the gasket.

4. The drug solution administration device according to claim 1, wherein the microcomputer is configured to rotate the motor forward after waiting for a lapse of a predetermined period after reversely rotating the motor.

5. The drug solution administration device according to claim 4, wherein the predetermined period is a period from when the motor is reversely rotated to when movement of the gasket is stopped.

6. The drug solution administration device according to claim 1, wherein the microcomputer is configured to determine that a failure occurs in the motor when the pusher does not move backward when the motor is started to reversely rotate.

7. A drug solution administration device comprising:
a drug solution container filled with a drug solution;
a gasket configured to be slidable on an inner wall in the drug solution container;
a pusher configured to push the gasket;
a drive mechanism configured to move the pusher forward and backward with respect to a distal end opening of the drug solution container;
a microcomputer configured to control operation of the drive mechanism;
wherein the drive mechanism includes a motor configured to generate driving force for moving the pusher forward and backward, and an encoder configured to detect rotation of the motor;
the microcomputer including an operation confirmation function configured to confirm an operating condition of the motor based on a detection result of the unit encoder;
the microcomputer is configured to determine whether or not the pusher is in contact with the gasket by reversely rotating the motor to cause the pusher to move backward and subsequently rotating the motor forward after confirming that the motor is stopped by the operation confirmation function.

8. The drug solution administration device according to claim 7, wherein the microcomputer is configured to determine whether or not the pusher is in contact with the gasket based on a value of a current flowing through the motor or rotation speed of the motor.

9. The drug solution administration device according to claim 7, wherein the microcomputer is configured to determine whether administration of the drug solution within the drug solution container is completed or blockage occurs, based on whether or not the pusher is in contact with the gasket.

10. The drug solution administration device according to claim 9, wherein the microcomputer is configured to rotate the motor forward after waiting for a lapse of a predetermined period after reversely rotating the motor.

11. The drug solution administration device according to claim 10, wherein the predetermined period is a period from when the motor is reversely rotated to when movement of the gasket is stopped.

12. The drug solution administration device according to claim 7, wherein the microcomputer is configured to determine that a failure occurs in the motor when the pusher does not move backward when the motor is started to reversely rotate.

* * * * *